United States Patent
Bacher et al.

(10) Patent No.: US 10,624,661 B2
(45) Date of Patent: Apr. 21, 2020

(54) TOOL FOR A MICRO-INVASIVE SURGICAL INSTRUMENT

(75) Inventors: Uwe Bacher, Tuttlingen (DE); Daniel Kaercher, Radolfzell (DE); Jochen Stefan, Wald (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 470 days.

(21) Appl. No.: 13/594,232

(22) Filed: Aug. 24, 2012

(65) Prior Publication Data

US 2013/0053835 A1  Feb. 28, 2013

(30) Foreign Application Priority Data

Aug. 24, 2011  (DE) .................. 10 2011 081 464

(51) Int. Cl.
  *A61B 17/29*  (2006.01)
  *A61B 17/00*  (2006.01)

(52) U.S. Cl.
  CPC .... *A61B 17/29* (2013.01); *A61B 2017/00464* (2013.01); *A61B 2017/2904* (2013.01); *A61B 2017/2929* (2013.01); *A61B 2017/2931* (2013.01)

(58) Field of Classification Search
  USPC ...................................................... 606/1, 205
  See application file for complete search history.

(56) References Cited

U.S. PATENT DOCUMENTS

| | | | |
|---|---|---|---|
| 4,817,847 A * | 4/1989 | Redtenbacher | A61B 17/1155 227/19 |
| 4,951,677 A * | 8/1990 | Crowley et al. | 600/463 |
| 5,053,043 A * | 10/1991 | Gottesman et al. | 606/148 |
| 5,275,614 A * | 1/1994 | Haber | A61B 17/0469 606/139 |
| 5,281,235 A * | 1/1994 | Haber et al. | 606/139 |
| 5,304,203 A * | 4/1994 | El-Mallawany et al. | 606/207 |
| 5,308,358 A * | 5/1994 | Bond | A61B 17/29 606/170 |
| 5,334,198 A * | 8/1994 | Hart | A61B 17/0467 606/52 |

(Continued)

FOREIGN PATENT DOCUMENTS

| | | |
|---|---|---|
| DE | 1929619 U | 12/1965 |
| DE | 7607219 U1 | 7/1976 |

(Continued)

OTHER PUBLICATIONS

The American Heritage(R) Dictionary of the English Language, Definition of "ball-and-socket joint", 2000.*

(Continued)

*Primary Examiner* — Carl H Layno
*Assistant Examiner* — Manolis Pahakis
(74) *Attorney, Agent, or Firm* — Whitmyer IP Group LLC

(57) ABSTRACT

A shaft for a micro-invasive surgical instrument includes a shaft tube with a proximal end portion and a distal end portion, a coupling device for detachable mechanical coupling of the shaft with a tool, and a rotation bearing, which mechanically connects the coupling device with the distal end portion of the shaft tube. The rotation bearing is configured in order to allow rotation of the coupling device with respect to the shaft tube about the longitudinal axis of the shaft on the distal end portion of the shaft.

10 Claims, 4 Drawing Sheets

(56) References Cited

U.S. PATENT DOCUMENTS

| | | | | |
|---|---|---|---|---|
| 5,368,606 | A * | 11/1994 | Marlow | A61B 17/29 606/170 |
| 5,405,344 | A * | 4/1995 | Williamson et al. | 606/1 |
| 5,499,992 | A * | 3/1996 | Meade et al. | 606/170 |
| 5,551,448 | A * | 9/1996 | Matula | A61B 50/30 128/897 |
| 5,593,402 | A * | 1/1997 | Patrick | 606/1 |
| 5,601,224 | A * | 2/1997 | Bishop et al. | 227/175.1 |
| 5,607,449 | A * | 3/1997 | Tontarra | A61B 17/29 606/205 |
| 5,626,587 | A * | 5/1997 | Bishop et al. | 606/143 |
| 5,643,294 | A * | 7/1997 | Tovey et al. | 606/148 |
| 5,662,588 | A * | 9/1997 | Iida | 600/121 |
| 5,676,678 | A * | 10/1997 | Schad | A61B 17/29 606/170 |
| 5,718,714 | A * | 2/1998 | Livneh | 606/205 |
| 5,782,748 | A * | 7/1998 | Palmer | A61B 10/06 600/104 |
| 5,792,165 | A * | 8/1998 | Klieman | A61B 17/29 606/170 |
| 5,810,879 | A * | 9/1998 | de Guillebon | A61B 17/29 600/564 |
| 5,817,128 | A * | 10/1998 | Storz | 606/205 |
| 5,893,875 | A * | 4/1999 | O'Connor | A61B 17/29 606/167 |
| 5,954,259 | A * | 9/1999 | Viola | A61B 17/07207 227/176.1 |
| 6,001,114 | A * | 12/1999 | Ouchi | 606/167 |
| 6,048,336 | A * | 4/2000 | Gabriel | 604/211 |
| 6,056,735 | A * | 5/2000 | Okada et al. | 606/1 |
| 6,126,359 | A * | 10/2000 | Dittrich | A61B 17/29 403/325 |
| 6,340,365 | B2 * | 1/2002 | Dittrich et al. | 606/205 |
| 6,547,798 | B1 * | 4/2003 | Yoon et al. | 606/141 |
| 7,338,513 | B2 * | 3/2008 | Lee et al. | 606/205 |
| 2002/0082640 | A1 * | 6/2002 | Scholer | A61B 17/29 606/205 |
| 2003/0050649 | A1 * | 3/2003 | Brock et al. | 606/130 |
| 2003/0114839 | A1 * | 6/2003 | Looper | A61B 17/320016 606/1 |
| 2003/0120272 | A1 * | 6/2003 | Schneider | A61B 17/00234 606/49 |
| 2003/0236549 | A1 | 12/2003 | Bonadio et al. | |
| 2004/0267254 | A1 * | 12/2004 | Manzo | A61B 18/14 606/39 |
| 2005/0096694 | A1 * | 5/2005 | Lee | 606/205 |
| 2005/0127131 | A1 * | 6/2005 | Mastri | A61B 17/0684 227/176.1 |
| 2006/0048787 | A1 * | 3/2006 | Manzo | 128/898 |
| 2006/0058581 | A1 * | 3/2006 | Hanke | 600/109 |
| 2006/0226195 | A1 * | 10/2006 | Scirica | A61B 17/07207 227/175.1 |
| 2007/0049966 | A1 * | 3/2007 | Bonadio et al. | 606/206 |
| 2007/0073247 | A1 * | 3/2007 | Ewaschuk | A61B 17/29 604/264 |
| 2007/0260257 | A1 * | 11/2007 | Phan | A61B 17/1617 606/84 |
| 2008/0004656 | A1 * | 1/2008 | Livneh | A61B 17/29 606/205 |
| 2008/0021278 | A1 * | 1/2008 | Leonard | A61B 17/1608 600/129 |
| 2008/0046001 | A1 * | 2/2008 | Renger et al. | 606/205 |
| 2008/0083808 | A1 * | 4/2008 | Scirica | A61B 17/07207 227/175.1 |
| 2008/0262480 | A1 * | 10/2008 | Stahler et al. | 606/1 |
| 2009/0171147 | A1 * | 7/2009 | Lee et al. | 600/104 |
| 2009/0240274 | A1 * | 9/2009 | Boebel | A61B 17/29 606/174 |
| 2009/0299143 | A1 * | 12/2009 | Conlon et al. | 600/153 |
| 2011/0106144 | A1 * | 5/2011 | Schweitzer et al. | 606/205 |
| 2011/0230867 | A1 * | 9/2011 | Hirschfeld | A61B 17/0469 606/1 |
| 2011/0295269 | A1 * | 12/2011 | Swensgard | A61B 17/068 606/130 |
| 2011/0306952 | A1 * | 12/2011 | Chen | A61B 17/29 606/1 |
| 2011/0313432 | A1 * | 12/2011 | Miles | A61B 17/1285 606/142 |
| 2012/0078292 | A1 * | 3/2012 | Banju | 606/206 |
| 2012/0116433 | A1 * | 5/2012 | Houser | A61B 18/1206 606/169 |
| 2012/0239010 | A1 * | 9/2012 | Shelton, IV | A61B 17/1155 606/1 |
| 2012/0253330 | A1 * | 10/2012 | Ries | A61B 17/162 606/1 |
| 2012/0259319 | A1 * | 10/2012 | Stefan et al. | 606/1 |
| 2013/0253499 | A1 * | 9/2013 | Kimball | A61B 18/1206 606/33 |
| 2013/0310814 | A1 * | 11/2013 | Bacher | A61B 17/00 606/1 |

FOREIGN PATENT DOCUMENTS

| | | |
|---|---|---|
| DE | 9317535 U1 | 1/1994 |
| DE | 102006038516 A1 | 2/2008 |
| DE | 102008015418 A1 | 9/2009 |
| DE | 102008052623 A1 | 4/2010 |
| WO | 9834543 A1 | 8/1998 |
| WO | 9903405 A2 | 1/1999 |
| WO | 0207611 A2 | 1/2002 |

OTHER PUBLICATIONS

German Search Report; Application No. DE 10 2011 081 464.7; dated Jun. 1, 2012; 5 pages.

* cited by examiner

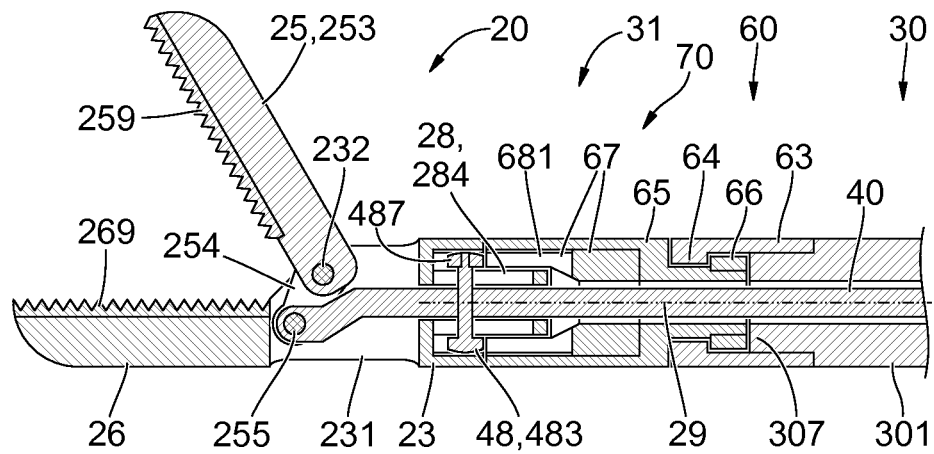
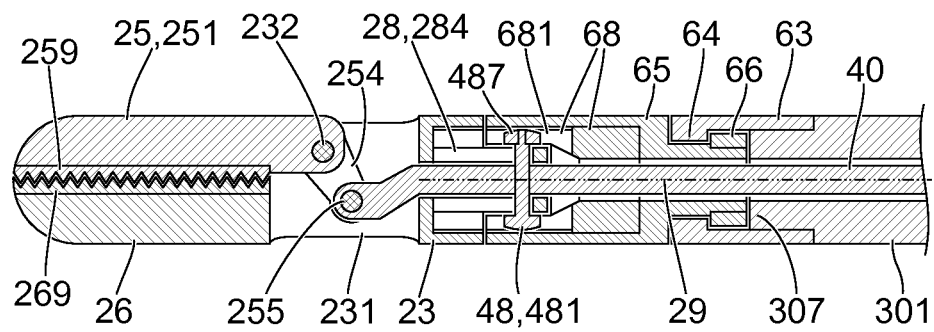
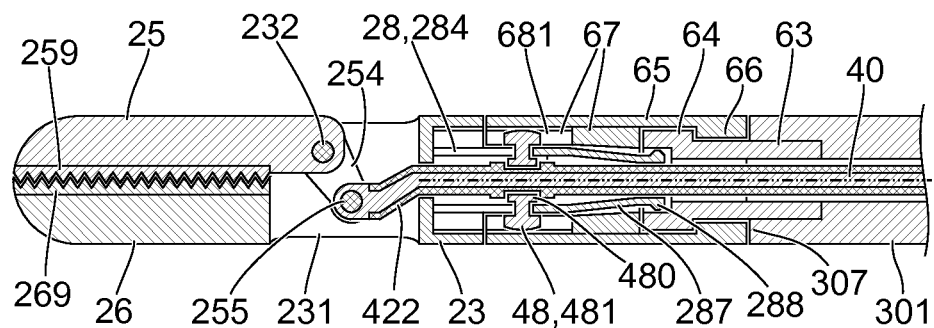
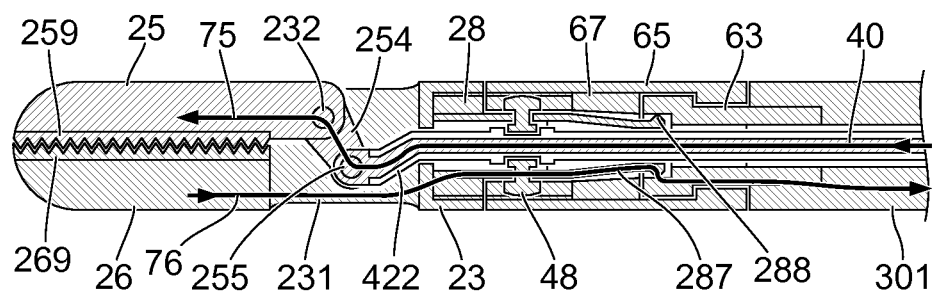

TOOL FOR A MICRO-INVASIVE SURGICAL INSTRUMENT

CROSS-REFERENCE TO RELATED APPLICATIONS

The present application claims priority of German patent application No. 10 2011 081 464.7 filed on Aug. 24, 2011, the content of which is incorporated herein by reference.

FIELD OF THE INVENTION

The present invention relates to a shaft for a micro-invasive surgical instrument, a micro-invasive surgical instrument, and at the same time, in particular, to the ability to rotate a tool on the distal end portion of the shaft.

BACKGROUND OF THE INVENTION

Many micro-invasive surgical instruments include a long, thin shaft, a tool on the distal end portion of the shaft and a handling device on the proximal end portion of the shaft. The tool includes, for example, a grasping, dissecting, biopsy or other forceps, a scissors or a needle holder with at least two straight or curved clamps, cutting edges or other jaw members of which at least one is movable. Alternatively, the tool includes another active device, for example a manipulator with a finger or a finger-shaped device or an electrode in hook form or other shape. The shaft contains (at least) one transmission rod, which as a rule is mounted in a closed channel in the interior of the shaft. The handling device includes one or more actuation devices that can move with respect to one another, for example two gripping parts, that medical staff can move in relation to one another with one hand. The proximal end portion and the distal end portion of the transmission rod are coupled with the actuation device or with the tool in such a way that a force exerted by medical staff onto the actuation devices or a relative movement of the actuation devices caused by medical staff can be transmitted to the tool, for example to move clamps toward one another or to press them together.

In using a micro-invasive surgical instrument of this type, the tool and a part of the shaft are inserted into a natural or artificial cavity in the patient's body, for example through a natural or artificial bodily opening. The development of micro-invasive surgical techniques tends toward using constantly smaller and, especially, fewer means of access. For example, in order to be able to work with an endoscope and two instruments in laparoscopic surgery by way of a single trocar, instruments with curved shafts can be used. An instrument with a curved shaft, however, cannot always be easily rotated around its longitudinal axis inside the access way in order to modify the orientation of the tool at its distal end portion.

In patent DE 10 2006 038 516 A1, a tubular medical instrument is described in which a tool 5, a shaft 3 and a handle 2 can be separated from one another for cleaning.

Patent DE 10 2008 015 418 A1 discloses a medical instrument with a curved shaft. A jaw member is detachably connected with a shaft by means of a bayonet lock. In connected position, the jaw member can be rotated with respect to the shaft. The shaft is detachably connected with a handle. The curved shaft can be rotated with respect to the handle by means of a hand wheel that is connected with an external shaft tube in torque-proof manner. An inside tube is connected to the handle with an additional hand wheel. The instrument can be configured as a unipolar or bipolar HF instrument.

Patent DE 10 2008 052 623 A1 discloses a surgical instrument with a jaw unit, a shaft and a gripping unit. The jaw unit is detachably affixed to the end of a shaft tube of the shaft and can rotate with respect to it.

To allow easy, thorough cleaning of the instrument, the tool, shaft and handling device of a micro-invasive surgical instrument, without use of auxiliary means, ought to be separable from one another and capable of being combined or coupled with one another. It is known, for example, from DE 10 2006 038 516 A1 how to configure the tool and the distal end portion of the shaft in such a way that the tool can be assembled and disassembled in a fully open assembled position. However, a few aspects both of the coupling of the tool with the shaft and of the coupling of the shaft with the handling device have not been sufficiently satisfactorily resolved to date, especially concerning the ability of the tool to turn or rotate with respect to the shaft when in coupled state.

SUMMARY OF THE INVENTION

An object of the present invention comprises providing an improved tool for a micro-invasive surgical instrument and an improved micro-invasive surgical instrument.

This object is achieved by the present teachings.

Refinements are indicated in various embodiments.

Embodiments of the present invention are based on the idea of implementing the ability to rotate a tool of a micro-invasive surgical instrument on the distal end portion of the shaft instead of on the tool. Depending on the configuration in detail, this can make a series of advantages possible. In particular, a part of the mechanical complexity of the tool can be displaced to the shaft. This can make it more economical to produce the tool. This is advantageous above all if many different tools are intended to be combined in alternation with one or a few shafts. An additional advantage includes the fact that a rotation bearing can become easier to integrate into the distal end portion of a shaft, which in many cases is mechanically less complex, than to integrate it into a tool that is often mechanically clearly more complex. An additional advantage includes the fact that the coupling between the tool and shaft can move closer to the distal end of the tool, so that when the tool is used as intended, moments that are to be absorbed by the coupling can be reduced.

One embodiment of a shaft for a micro-invasive surgical instrument includes a shaft tube with a proximal end portion and a distal end portion, a coupling device for detachable mechanical coupling of the shaft with a tool, and a rotation bearing, which mechanically connects the coupling device with the distal end portion of the shaft tube, such that the rotation bearing is configured to make possible a rotation of the coupling device in relation to the shaft tube about the longitudinal axis of the distal end portion of the shaft.

The shaft tube can be mechanically connectable, or connected, directly or indirectly with a handling device. An indirect connection of the shaft tube with a handling device includes, for example, a coupling device that is joined with the shaft tube and comprises one or more grooves or studs for mechanical catch-locking with the handling device. In addition, the shaft tube can be separable from the handling device, on a durable basis and not free of disturbance, without the use of the tool. The shaft tube can be mechanically connectable, or connected, with a handling device in such a way that it can be rotated with respect to the handling device around its longitudinal axis on the proximal end portion.

The shaft tube may comprise in particular a central channel for inserting a rigid or pliable transmission rod, such that the central channel extends over the entire length from the proximal end to the distal end of the shaft tube. Both the shaft tube and the channel each may have, in particular, a circular cross-section or a cross-section with a circular border.

The coupling device may be configured in particular to allow both a mechanical coupling and a release of the mechanical coupling without use of tool and without disturbance. The handling of the entire micro-invasive surgical instrument by medical and other staff can thereby be simplified both before and after use as well as in the cleaning and sterilization processes.

The mechanical connection provided by the rotation bearing between the coupling device and the distal end portion of the shaft tube may not be released, in particular, free of disturbance without a tool. The rotation bearing may be configured in particular exclusively to allow a rotation of the coupling device in relation to the shaft tube about the longitudinal axis of the shaft—in the case of a curved shaft, about the longitudinal axis of the distal end portion of the shaft or about the longitudinal axis of the shaft at its distal end portion. For this purpose, the rotation bearing may be configured in such a way that it prevents all three translational degrees of freedom and two out of three rotational degrees of freedom—apart from mechanical play.

In a shaft as described here, the rotation bearing may be, in particular, configured as a Radiax bearing.

A Radiax bearing is a combination of a radial bearing, which prevents the two translational degrees of freedom perpendicular to the longitudinal axis and the rotational degrees of freedom about both directions perpendicular to the longitudinal axis, and an axial bearing that prevents the translational degree of freedom parallel to the longitudinal axis. As a result of this configuration, the rotation bearing restricts the movement of the coupling device in relation to the shaft tube to just a single rotational degree of freedom.

In a shaft as described here, the rotation bearing can include a collar extending radially inward and a collar extending radially outward, such that either the collar extending radially outward is rigidly connected with the coupling device and the collar extending radially inward is rigidly connected with the distal end portion of the shaft tube, or vice versa.

The two collars may be, in particular, each circular in shape and positioned symmetrically to the longitudinal axis of the shaft at its distal end portion. The collar extending radially inward may engage in a groove opening radially outward with corresponding cross-section whose one flank is configured by the collar extending radially outward. The collar extending radially outward may engage in a groove opening radially inward with corresponding cross-section whose one flank is configured by the collar extending radially inward. In other words, the collars may reach behind one another in such a way that the two collars have the capacity to rotate with respect to one another with low friction, and thereby the same is true of the coupling device and the distal end of the shaft tube with respect to one another. Thus the collars can each have a lesser extension in the radial direction than in the axial direction.

In particular, the embodiments presented with reference to the appended drawings show that two collars reaching behind one another in axial direction can form a rotation bearing that is robust, low in play and low in friction.

A shaft as described here may be, in particular, curved.

The shaft can be curved in a plane, such that the center points of all cross-sections of the shaft are situated on a level curve or a curve in one plane. Alternatively, the shaft can be curved three-dimensionally, such that the center points of all cross-sections of the shaft are situated on a curve that is not level.

The longitudinal axis of the shaft or of another object is intended here in particular to mean the axis to which the particular object is rotation-symmetrical or essentially rotation-symmetrical. In the case of a curved or elastic shaft or other object, these comments apply in particular to their ends, which are in particular straight or not curved, at least in parts.

A shaft as described here may be in particular configured to be coupled with a tool that is provided for a coupling with a shaft without rotation bearing.

The shaft may be therefore, in particular, intended and configured for a combination or use with a conventional tool, which is intended for a conventional use without ability to rotate. Thus the shaft makes possible the ability to rotate, which, as described before, is important for some uses, including for use with conventional tools, which are already available, for example, among the inventory of a clinic or other medical facility. The shaft can thus make possible, at comparatively low cost, a substantial improvement in the functionality of micro-invasive surgical instruments. In particular, the coupling device of the shaft may be configured for coupling with a conventional tool.

In a shaft as described here, the coupling device may be configured in particular to allow locking of a mechanical coupling with a tool.

For this purpose the coupling device may comprise, in particular, an axial groove or an axial slit, into which a locking device connected with a tool can engage, in order to lock the coupling of the tool with the coupling device of the shaft.

In a shaft as described here, the coupling device may comprise, in particular, a groove or slit with an axial portion and a peripheral portion for insertion of a cam on a tool.

An axial portion is a portion that extends in the axial direction or essentially in the axial direction. A peripheral portion is a portion that extends in peripheral direction or essentially in peripheral direction. The axial portion and the peripheral portion may be, in particular, positioned in an L-shaped arrangement, so that the proximal end of the axial portion merges into an end of the peripheral portion or is identical with it. A cam can be inserted into a groove of this kind or a slit of this kind, by an axial movement and a subsequent rotational movement of the tool in relation to the coupling device. The coupling device can comprise two or more grooves or slits, which are distanced from one another in particular at equal angles in order to simplify coupling of the tool and the coupling device and to improve the mechanical robustness of the coupling.

A shaft as described here can, in addition, comprise a sleeve component with a distal portion that configures the coupling device and a proximal portion that configures a part of the rotation bearing.

The sleeve component can include several coaxial sleeves to simplify production. For example, the inner sleeve can comprise a groove or a slit as described above and be joined with an outer, coaxial sleeve.

A micro-invasive surgical instrument may include a shaft as described above and a tool, which can be detachably mechanically coupled with the coupling device on the distal end of the shaft.

A micro-invasive surgical instrument as described here can, in addition, include a handling device, which can be coupled or is coupled with the proximal end of the shaft, such that the handling device comprises an actuation device to rotate a transmission rod, which is positioned in the shaft and whose distal end portion is coupled with the tool.

The actuation device is configured in particular for manual or mechanical rotation of a proximal end portion or of a proximal area of the transmission rod.

BRIEF DESCRIPTION OF THE DRAWINGS

Hereinafter, embodiments are presented in greater detail with reference to the appended drawings, which are as follows.

FIG. 10 shows a schematic depiction of a shaft with an additional tool.

FIG. 11 shows another schematic depiction of the shaft from FIG. 10.

FIG. 12 shows a schematic depiction of an additional shaft with a tool.

FIG. 13 shows an additional schematic depiction of the shaft from FIG. 12.

DETAILED DESCRIPTION OF THE INVENTION

Figure 1:
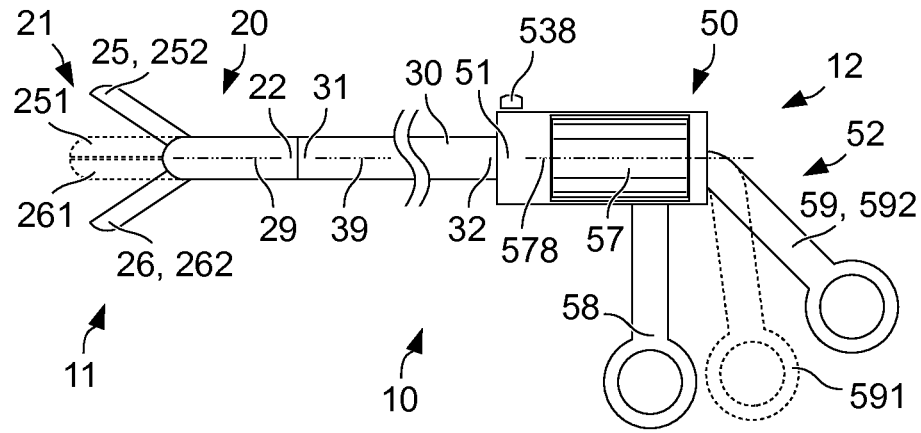
FIG. 1 shows a schematic depiction of a micro-invasive surgical instrument.

FIG. 1 shows a schematic depiction of one embodiment of a micro-invasive surgical instrument 10 with a distal end portion 11 and a proximal end portion 12. The micro-invasive surgical instrument 10 includes a tool 20, a shaft 30 and a handling device 50. On the distal end portion 21 the tool 20 comprises a first movable jaw member 25 and a second movable jaw member 26. Said jaw members 25, 26 are depicted in FIG. 1 in solid lines in open positions 252, 262 and in broken lines in closed positions 251, 261. The jaw members 25, 26 can each be straight or essentially straight, or curved in the direction perpendicular to the plane of projection of FIG. 1 and/or—contrary to the depiction in FIG. 1—in the plane of projection of FIG. 1.

The proximal end portion 22 of the tool 20 is detachably mechanically coupled with a distal end portion 31 of the shaft 30. The shaft 30 is shown strongly shortened in FIG. 1 and straight, for the sake of brevity. Departing from the depiction in FIG. 1, the shaft 30 can be level or spatially curved. With a shape of the shaft 30 that is curved within a plane or—even more advantageous for some uses—spatially curved, the micro-invasive surgical instrument 10 can be suited especially for micro-invasive surgical interventions in which an endoscope and one or more instruments can be inserted simultaneously through a single access into a body cavity.

The proximal end portion 32 of the shaft 30 is detachably mechanically coupled with the distal end portion 51 of the handling device 50. To handle the micro-invasive surgical instrument 10, the handling device 50 comprises a rotary wheel 57, a first gripping member 58 and a second gripping member 59. The rotary wheel 57 is provided to guide a rotation of the tool 20, in particular of the jaw members 25, 26, about a longitudinal axis 29. In the example shown in FIG. 1, the rotary wheel 57 can rotate about an axis 578, which simultaneously is the longitudinal axis of the shaft 30 at its proximal end portion 32. Alternatively, the axis 578 can be parallel to the longitudinal axis of the shaft 30 at its proximal end portion 32. In addition, the rotary wheel 57 comprises a surface structure, which makes possible a reliable operation or actuation even with gloves, for example the studs indicated in the axial direction. The gripping members 58, 59, in particular—contrary to the highly stylized shape shown in FIG. 1—are disposed and shaped in such a way that medical staff can grip both gripping members 58, 59 and move them with respect to one another with one hand, with minor fatigue resulting.

At least one of the two gripping members 58, 59 is movable with respect to the other components of the handling device 50. In the example shown in FIG. 1, the first gripping member 58 is disposed rigidly and the second gripping member 59 movably. In particular, the second gripping member 59 can move between a first working position 591, shown in broken lines in FIG. 1, and a second working position 592, shown in solid lines in FIG. 1. The second gripping member 59 of the handling device 50 is mechanically coupled with the jaw members 25, 26 of the tool 20 in such a way that the jaw members 25, 26 are situated in their closed positions 251, 261 if the second gripping member 59 assumes its first working position 591, and so that the jaw members 25, 26 are situated in their open positions 252, 262 if the second gripping member 59 assumes its second working position 592.

Figure 2:
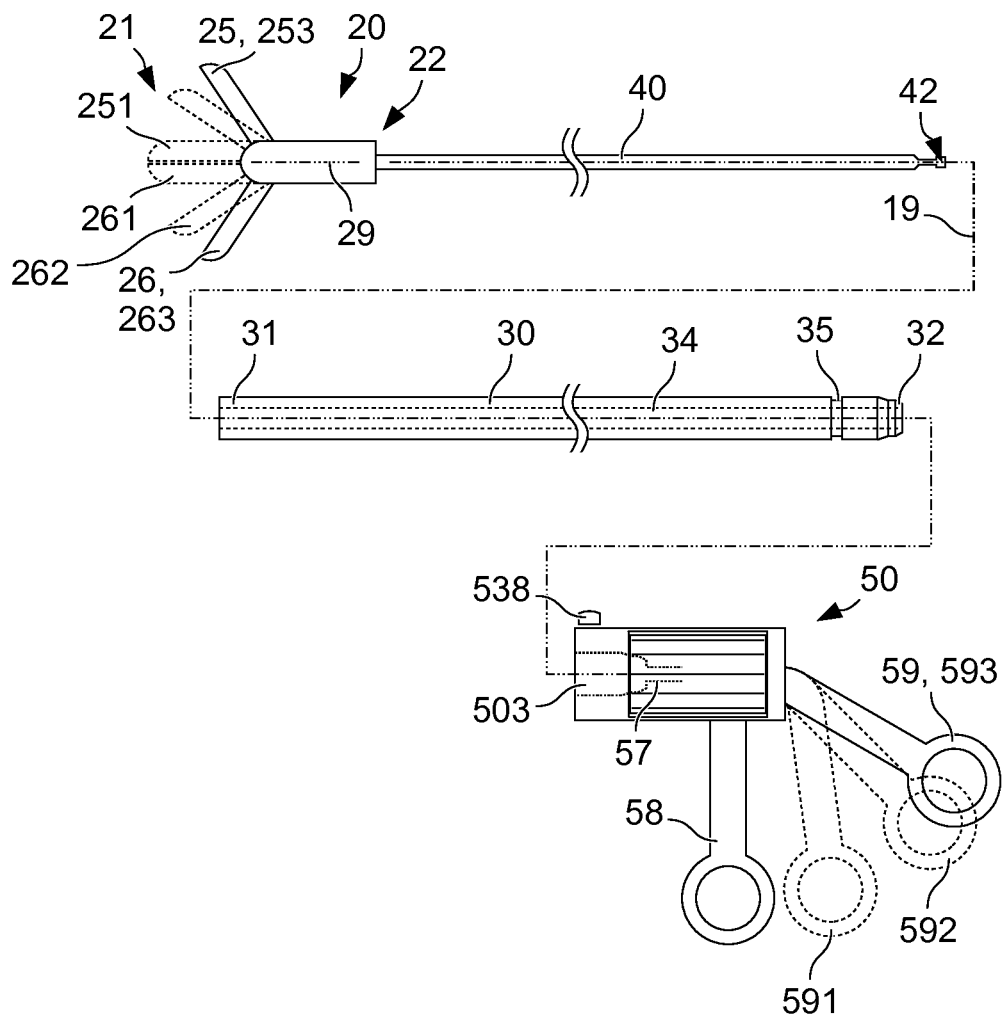
FIG. 2 shows a schematic depiction of the micro-invasive surgical instrument from FIG. 1 in dismantled form.

FIG. 2 shows a schematic depiction of components of the micro-invasive surgical instrument 10, which is described above with reference to FIG. 1; said components can be assembled or joined to the instrument without use of a tool. The micro-invasive surgical instrument 10 can likewise be dismantled into the components shown separately in FIG. 2 without a tool. The line 19 shown in dots and dashes that runs throughout FIG. 2 indicates how these components are put together.

The tool 20 is, in particular, durably connected with a transmission rod 40, which is intended for transmission of a force and torque from the handling device 50 to the tool 20. The distal end portion of the transmission rod 40, not shown in FIG. 2, is coupled with the jaw members 25, 26 in such a way that a movement of the transmission rod 40 parallel to the longitudinal axis 29 of the tool 20 causes a synchronous movement of the jaw members 25, 26.

Bayonet coupling devices, not shown in FIG. 2, as well as a locking device coupled with the transmission rod 40 are provided on the proximal end portion 22 of the tool 20 and on the distal end portion 31 of the shaft 30. The jaw members 25, 26 are depicted in FIG. 2 in solid lines in fully open positions 253, 263 and in broken lines in the closed and open positions 251, 252, 261, 262 already described above with reference to FIG. 1. If the jaw members 25, 26 are situated in the fully open positions 253, 263, the locking device, which is coupled with the jaw members 25, 26 and the distal end portion of the transmission rod 40 and is not shown in FIG. 2, is inactive. In this condition, the transmission rod 40 can be inserted into a channel 34 foreseen for the transmission rod 40 in the shaft 30, and the proximal end portion 22 of the tool and the distal end portion 31 of the shaft can be detachably mechanically connected or coupled with one another by the bayonet coupling devices, which are not shown in FIG. 2. In addition, in this unlocked condition a mechanical coupling of the proximal end portion 22 of the tool 20 and of the distal end portion 31 of the shaft 30 can be detached by the bayonet coupling devices, which are not shown in FIG. 2.

If the jaw members 25, 26 are situated in the closed positions 251, 261, in the open positions 252, 262 or in positions lying between them, the locking device, which is coupled with the distal end portion of the transmission rod 40 and indirectly with the jaw members 25, 26, is situated in a working position or in a position within a working range. In the working position or in positions within the working range, the mechanical coupling of the proximal end portion 22 of the tool 20 is locked with the distal end portion 31 of the shaft 30 by the bayonet coupling devices, which are not shown in FIG. 2. If the mechanical connection or coupling of the tool 20 and shaft 30 is locked, the tool 20 and the shaft 30 cannot be separated from one another, or not necessarily without disturbance.

Instead of the bayonet coupling devices, the proximal end portion 22 of the tool 20 and the distal end portion 31 of the shaft 30 can comprise other coupling devices. In this case as well, a locking device can be provided on the tool 20 that locks the mechanical connection of the tool 20 and shaft 30 if the jaw members 25, 26 are situated in the fully open positions 253, 263.

If the transmission rod 40 is inserted into the channel 34 of the shaft 30 and the proximal end portion 22 of the tool 20 is mechanically connected or coupled with the distal end portion 31 of the shaft 30, the proximal end portion 32 of the shaft 30 can be inserted into the handling device 50 with the proximal end portion 42 of the transmission rod 40, which extends beyond the proximal end of the shaft 30. For this purpose the handling device 50 comprises a recess 503, which is indicated in FIG. 2 by a dotted line.

To insert the proximal end portion 32 of the shaft 30 and the proximal end portion 42 of the transmission rod 40 into the handling device 50, the second gripping member 59 is first brought into a coupling position 593, indicated in FIG. 2 in solid outline. If the second gripping member 59 is situated in the coupling position 593, then a rod coupling, not shown in FIG. 2, is found inside the handling device 50 in a coupling position in which it can admit or release the proximal end portion 42 of the transmission rod 40. If the proximal end portion 42 of the transmission rod 40 is inserted completely into the handling device 50, the rod coupling, not shown in FIG. 2, inside the handling device 50 is mechanically connected or coupled with the proximal end portion 42 of the transmission rod 40. In the process, the second gripping member 59, depending on the positions of the jaw members 25, 26 (closed positions 251, 261, open positions 252, 262 or between the two), moves into the first working position 591, the second working position 592 or a position between the first working position 591 and the second working position 592.

If the proximal end portion 32 of the shaft 30 is inserted entirely into the handling device 50, a lock, not shown in FIG. 2, engages in a surrounding groove 35 close to the proximal end of the shaft 30 and thereby locks the proximal end portion 32 of the shaft 30 in a foreseen position in the handling device 50. Because of the locking of the proximal end portion 32 of the shaft 30 in the handling device 50, the mechanical coupling of the proximal end 42 of the transmission rod 40 is also indirectly locked with the rod coupling, not shown in FIG. 2, inside the handling device 50.

After locking the proximal end portion 32 of the shaft 30 in the handling device 50 and indirectly locking the proximal end portion 42 of the transmission rod 40 in the rod coupling, not shown in FIG. 2, in the handling device 50, the micro-invasive surgical instrument 10 is configured as shown in FIG. 1.

By moving the second gripping member 59 with respect to the first gripping member 58 between the two working positions 591, 592, the jaw members 25, 26 can be moved between the closed positions 251, 261 and open positions 252, 262. By rotating the rotary wheel 57 about the axis 578, the tool 20 and jaw members 25, 26 can be rotated about the longitudinal axis 29 of the tool 20. For this purpose a rotation bearing, not shown in FIGS. 1 and 2, is provided at or close to the distal end of the shaft 30.

Departing from the depictions in FIGS. 1 and 2, the shaft 30 close to its proximal end can comprise an additional rotary wheel, which is positioned close to the distal end of the handling device 50, if the proximal end portion 32 of the shaft 30 is inserted into the handling device 50. By means of this rotary wheel, not shown in FIGS. 1 and 2, the shaft 30 can be rotated about the longitudinal axis of the proximal end portion 20 of the shaft 30. This is particularly significant if the shaft 30, contrary to the depictions in FIGS. 1 and 2, is curved. In this case the curved shaft 30 and the tool 20 can be rotated on the distal end of the curved shaft 30 independently of one another.

By pressure on the unlocking button 538, the lock, not shown in FIG. 2, can be slid against the force of a spring and can be released from the groove 35 on the shaft 30. Then the proximal end portion 32 of the shaft 30 can be removed from the handling device 50. In the process, the locking of the proximal end portion 42 of the transmission rod 40 is also released on the rod coupling, not shown in FIGS. 1 and 2, in the handling device 50.

Instead of one or—as shown in FIGS. 1 and 2—two movable jaw members 25, 26, the tool 20 can comprise another active device, in particular a manipulator, for example a finger-shaped manipulator, or an electrode, for example a hook-shaped electrode.

Figure 3:
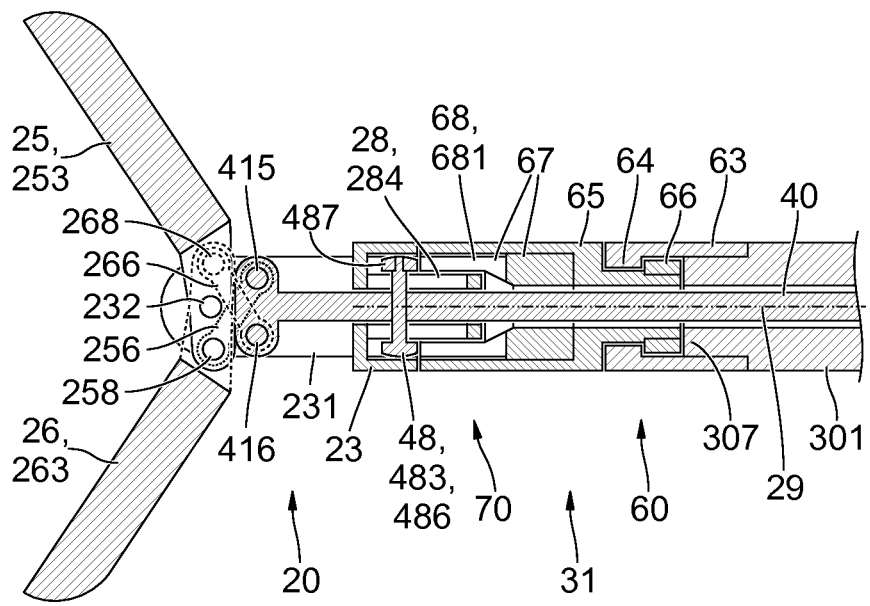
FIG. 3 shows a schematic depiction of a shaft with a tool.
Figure 4:
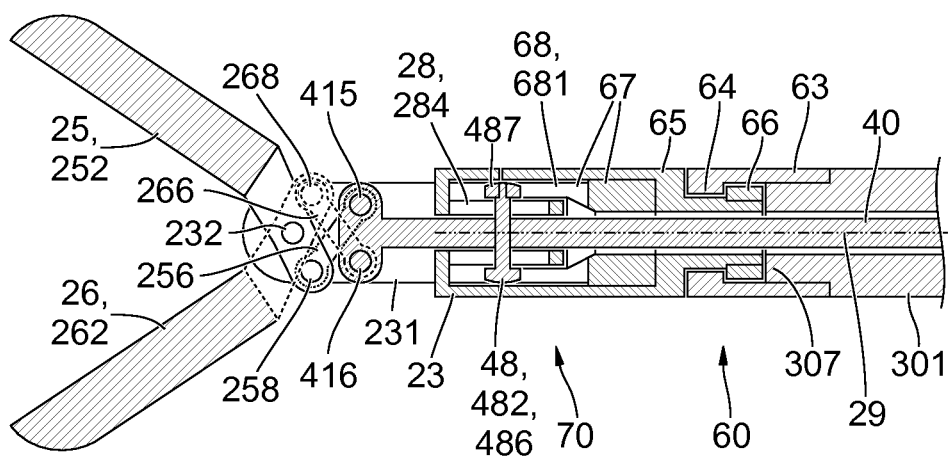
FIG. 4 shows another schematic depiction of the shaft from FIG. 3.
Figure 5:
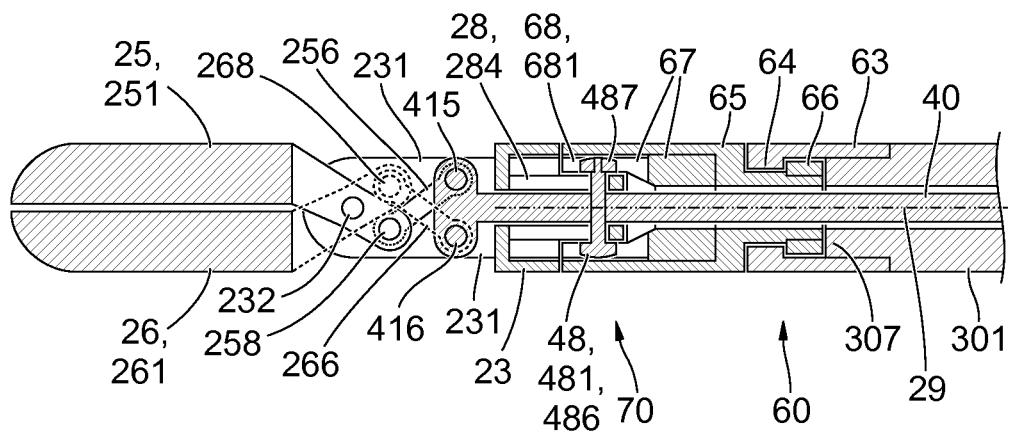
FIG. 5 shows another schematic depiction of the shaft from FIGS. 3 and 4.

FIGS. 3 through 5 show schematic sectional views of an embodiment of the tool 20 described above with reference to FIGS. 1 and 2 and of the distal end portion of the shaft 30 presented above with reference to FIGS. 1 and 2. The sectional planes of FIGS. 3 through 5 are parallel to the planes of projection of FIGS. 1 and 2 and contain the longitudinal axis 29 of the tool 20 indicated in FIGS. 1 and 2. The longitudinal axis 29 of the tool 20 is indicated by a dot-and-dash line in each of FIGS. 3 through 5. The longitudinal axis 29 of the tool 20 is the axis of symmetry of a few, but far from all, of the features of the tool 20. In addition, the longitudinal axis 29 of the tool coincides with the longitudinal axis of the shaft 30 or—if the shaft 30 is curved —with the longitudinal axis of the shaft on its distal end portion 31, shown in FIGS. 3 through 5.

The jaw members 25, 26 are shown in FIG. 3 in their fully open positions 253, 263, in which the mechanical connection between the tool 20 and shaft 30 is unlocked, that is, can be produced or released. The jaw members 25, 26 are shown in FIG. 4 in their open positions 252, 262; the connection between the tool 20 and shaft 30 is locked. In FIG. 5 the jaw members 25, 26 are shown in their closed positions 251, 261; the connection between the tool 20 and shaft 30 is likewise locked.

The transmission rod 40 comprises two joints 415, 416 on the distal end portion 41. A first piston rod 256 connects the first joint 415 on the distal end portion 41 of the transmission rod 40 with a joint 258 on the first jaw member 25 that is at a distance from an axle 232. A second piston rod 266 connects the second joint 416 on the distal end portion 41 of the transmission rod 40 with a joint 268 on the second jaw member 26 that is distanced from the axle 232. From a comparison of FIGS. 3 through 5 it can be recognized that a linear sliding of the transmission rod 40 parallel to the longitudinal axis 29 of the tool 20 by means of the piston rods 256, 266 causes a pivoting of the jaw members 25, 26 about the joints formed by the axle 232.

The tool 20 comprises a joint device 23, which is configured in a distal area as fork-shaped with two prongs. One prong 231 is situated behind the sectional planes of FIGS. 3 through 5 and can be recognized in FIGS. 3 through 5. A second prong is configured and positioned symmetrically to the prong 231 shown in FIGS. 3 through 5 with respect to the sectional planes of FIGS. 3 through 5. The second prong is situated in front of the sectional plane of FIGS. 3 through 5 and is therefore not shown in FIGS. 3 through 5. One end portion of the axle 232 positioned perpendicular to the sectional planes of FIGS. 3 through 5 is held or mounted in one of the two prongs 231 of the joint device 23.

The proximal end portion of the joint device 23 has approximately the shape of a circular-cylindrical mantle, which surrounds a distal end portion of a coupling component 28 and is, in particular, in a firmly bonded connection with it. Said coupling component 28 has a shape that is essentially rotation-symmetrical to the longitudinal axis 29 of the tool 20 with a central channel in which the transmission rod 40 is disposed. The coupling component 28, proximally from the joint device 23, has an essentially circular-cylindrical shape with a markedly reduced cross-section in comparison with the joint device 23.

In a departure from the rotation symmetry to the longitudinal axis 29 of the tool 20, the coupling component 28 comprises two axial slits 284, which starting from the distal end extend almost to the proximal end of the coupling component 28, and in which the sectional planes of FIGS. 3 through 5 are situated. A locking unit 48, which is disposed in the slits 284, is made up of a pin 486 and a ring-shaped cap 487. A thin cylindrical portion of the pin 486 is disposed in the transmission rod 40 in a borehole of corresponding cross-section perpendicular to the longitudinal axis 29 of the tool 20. On opposite sides of the transmission rod 40, one end portion each of the pin 486 extends out and engages in one of the two axial slits 284 in the coupling component 28. On an end portion, illustrated in each case in the lower part of FIGS. 3 through 5, the pin 486 has an enlarged cross-section. The cap 487 with corresponding cross-section is joined to the pin 486 at the opposite end portion.

In addition, the shape of the coupling component 28 departs from rotation symmetry at its proximal end portion because of two cams. These cams are situated outside the sectional planes of FIGS. 3 through 5 and therefore are not recognizable in these illustrations.

In an axial movement of the transmission rod 40 between the positions shown in FIGS. 3 through 5, the locking device 48 is moved between the installation position 483 shown in FIG. 3 and the working positions 482 or 481 shown in FIGS. 4 and 5. With the locking device 48 in the installation position 483, said device is positioned entirely inside the cylindrical mantle-shaped portion of the joint device 23. The slits 284 in the coupling component 28 have cross-sections that are adjusted in this area to the end portions of the locking device 48 in order to completely insert them. With the locking device 48 in the working positions 482 or 481 illustrated in FIGS. 4 and 5, the two end portions of the locking device 48 protrude in a direction perpendicular to the longitudinal axis 29 of the tool 20 and parallel to the sectional planes of FIGS. 3 through 5, at least partly, with respect to the coupling component 28, or extend outward from the slits 284 in the coupling component 28.

The shaft 30 includes a shaft tube 301 made of metal or other material. On the distal end portion 31 of the shaft 30 (compare FIGS. 1 and 2) shown in FIGS. 3 through 5, a collar component 63 with a collar 64 extending radially inward, an outer sleeve 65 with a collar 66 extending radially outward and an inner sleeve 67 with slits 68 are provided. The slits 68 in the inner sleeve 67 each comprise an axial portion 681 that can be recognized in FIGS. 3 through 5 and a peripheral portion that is not recognizable in FIGS. 3 through 5.

The collar component 63 is rotation symmetrical with the longitudinal axis 29 and has essentially the shape of a circular-cylindrical mantle. With the circular ring-shaped collar 64 extending radially inward, the collar component 63 departs from the shape of a circular cylindrical mantle. The proximal border of the collar component 63 is joined with the shaft tube 301 close to its distal end or on its distal end portion 307, in particular in a form-locked or firmly bonded connection.

The outer sleeve 65 is essentially rotation symmetrical with the longitudinal axis 29 of the tool 20. A distal area of the outer sleeve 65 has essentially the shape of a circular-cylindrical mantle, whose outer diameter corresponds to the outer diameters of the collar component 63 and of the shaft tube 301. A proximal area of the outer sleeve 65 has a reduced cross-section. The collar 66 extending radially outward on the proximal border of the outer sleeve 65, in the example shown in FIGS. 3 through 5, is configured by a ring-shaped component that is separately produced and then joined by force-locking, form-locking and/or firm bonding to the outer sleeve 65.

The collar 64 of the collar component 63 extending radially inward is positioned on the outer sleeve 65 in a circular-ring-shaped groove that opens radially outward and is of corresponding diameter. The proximal flank of this groove is configured by the collar 66 of the outer sleeve 65 that extends radially outward. The distal flank of the groove opening radially outward is configured by the step-shaped transition of the outer sleeve 65 to the aforementioned circular-cylindrical mantle-shaped distal area. The collar 66 on the outer sleeve 65 that extends radially outward is disposed in a groove of corresponding diameter between the distal end of the shaft tube 301 and the collar 64 on the collar component 63 that extends radially inward.

The reciprocal reaching behind of the collar 64 extending radially inward on the collar 63 and of the collar 66 extending radially outward on the outer sleeve 65, or the arrangement of the two collars 64, 66 in grooves of corresponding cross-section, provides a form-locked connection between the outer sleeve 65 on the one hand and the collar component 63 and shaft tube 301 on the other hand. This form-locked connection constitutes a rotation bearing—in particular a Radiax bearing—that allows a rotation of the outer sleeve 65 with respect to the collar component 63 and to the shaft tube 301 about the longitudinal axis 29 of the tool 20, with little play and friction, and prevents all other degrees of freedom completely or except for a minor amount of play.

The inner sleeve 67 is mounted in the circular-cylindrical mantle-shaped distal area of the outer sleeve 65 and joined to it by force-locking, form-locking and/or firm bonding. The shape of the slit 68 is adjusted to the shape of the cams on the proximal end portion of the coupling component 28 that are not visible in FIGS. 3 through 5, so that the cams can be inserted through the axial portions 681 into the peripheral portions of the slits 68 in the inner sleeve 67.

In the assembly position 483 of the locking device 48 shown in FIG. 3, the tool 20 can be rotated with respect to the sleeve component configured by the outer sleeve 65 and the inner sleeve 67 as far as the cams inside the peripheral portions of the slits 68 are movable in the inner sleeve 67. In particular, the tool 20 can be mounted on the distal end portion 31 of the shaft 30 by inserting the cams by a purely axial movement parallel to the longitudinal axis 29 of the tool 20 into the axial portions 681 as far as the peripheral portions of the slits 68 in the inner sleeve 67. By a subsequent rotation of the tool 20 with respect to the sleeve component formed by the sleeves 65, 67 about the longitudinal axis 29 of the tool 20, the cams are slid into areas of the peripheral portions of the slits 68 that are at a distance from the axial portion 681.

If the axial slits 284 in the coupling component 28 and the axial portions 681 of the slits 68 in the inner sleeve 67, as indicated in FIGS. 3 through 5, are situated in a plane, by an axial sliding of the transmission rod 40 the locking device 48 can be slid from the assembly position 483 shown in FIG. 3 into the working positions 482, 481 shown in FIGS. 4 and 5. With the locking device 48 in the working positions 482, 481 shown in FIGS. 4 and 5, the form-locking of the locking device 48, with the slits 284 in the coupling component 28 of the tool 20 on the one hand and with the axial portions 681 of the slits 68 in the inner sleeve 67 on the other hand, prevents relative rotation of the tool and of the sleeve component formed by the sleeves 65, 67. The connection between the tool 20 and shaft 30 formed mechanically by the form-locking between the cams and coupling component 28 of the tool 20 on the one hand and the peripheral portions of the slits 68 in the inner sleeves 67 on the other hand, is thus locked by the locking device 48. Simultaneously the rotation bearing 60 allows a rotation of the tool 20 with respect to the shaft 30 about the longitudinal axis 29 of the tool 20.

FIGS. 6 through 9 show schematic depictions of the coupling device 70, already introduced with respect to FIGS. 3 through 5, between the tool 20 and shaft 30. At the same time, FIGS. 6 through 9 show in solid outline, in each case, only the coupling component 28 of the tool 20, the inner sleeve 67 on the distal end portion 31 of the shaft 30, the transmission rod 40 and the locking device 48. The drawings omit, or show only in broken outline, the other devices and components, which are not directly involved in the coupling device 70 or in the coupling between the tool 20 and shaft 30. This is true in particular for the joint device 23 of the tool 20 with the prongs 231, 233, the shaft tube 301, the collar component 63 and the outer sleeve 65.

Shown in FIGS. 6 through 9, at left in each case, is a section along a plane A-A perpendicular to the longitudinal axis 29 of the tool 20 (compare FIGS. 1 through 5). FIGS. 6 through 9, at the right in each case, show an overhead view whose plane of projection in each case is parallel to the longitudinal axis 29 of the tool 20 and perpendicular to the planes of projection of FIGS. 1 through 5.

Figure 6:
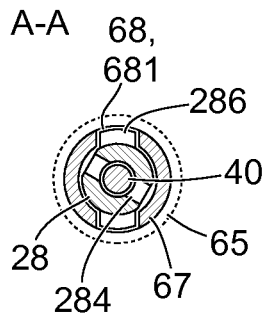
FIG. 6 shows a schematic depiction of coupling devices.
Figure 6:
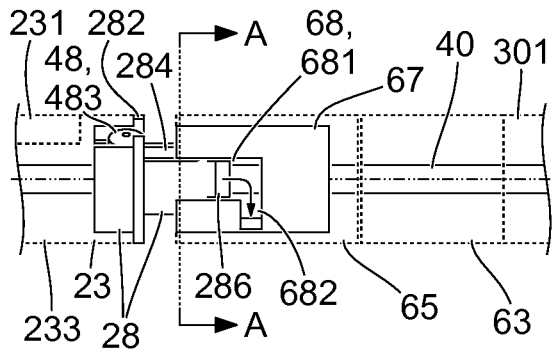

FIG. 6 shows an intermediate condition during the affixing of the tool 20 to the shaft 30, in which the cams 286 on the coupling component 28 are situated in the axial portions 681 of the L-shaped slits 681 in the inner sleeve 67. An arrow indicates the movement of the cams 286 up to the situation shown in FIG. 7. By an axial movement of the tool and of the coupling component 28 with respect to the inner sleeves 67 and a subsequent rotation (in the illustrated example: by an angle of approximately 60 degrees), the cams 286 are inserted through the axial portions 681 into the peripheral portions 682 of the slits 68 in the inner sleeve 67 until the coupling component 28 is completely contiguous with the inner sleeve 67 and the situation shown in FIG. 7 prevails.

Figure 7:
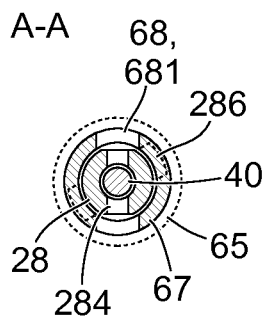
FIG. 7 shows an additional schematic depiction of the coupling devices from FIG. 6.
Figure 7:
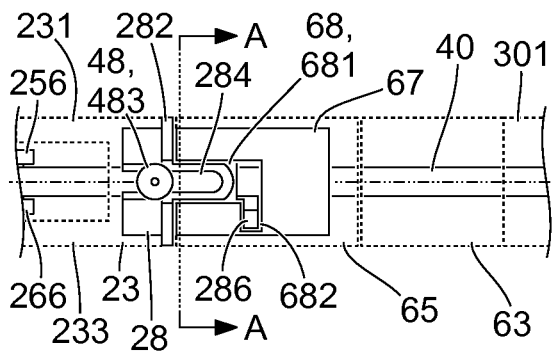
Figure 8:
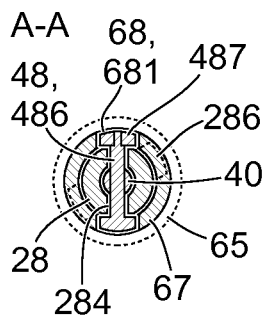
FIG. 8 shows an additional schematic depiction of the coupling device from FIGS. 6 and 7.
Figure 8:
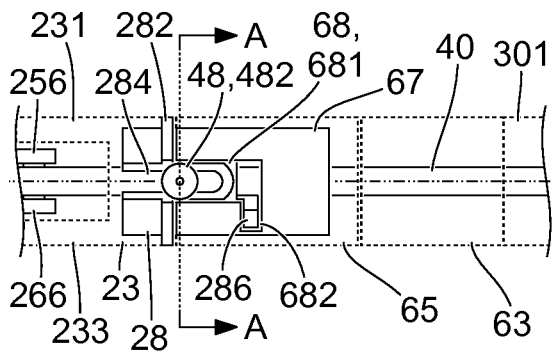
Figure 9:
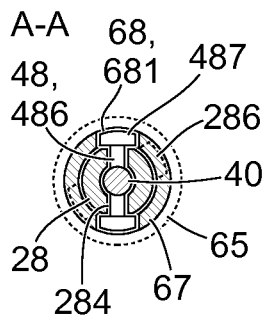
FIG. 9 shows another schematic depiction of the coupling devices from FIGS. 6 through 8.
Figure 9:
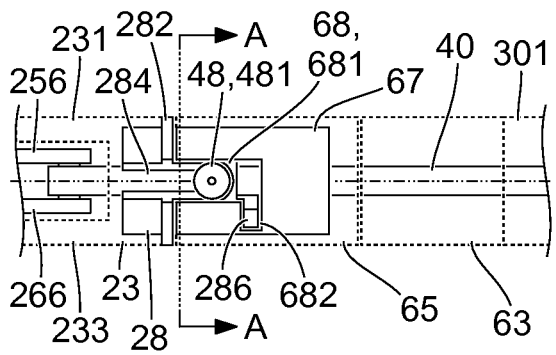

The situation shown in FIG. 7 is the same as that shown in FIG. 3, in which the locking device 48 is seen in its assembly position 483. In the situation shown in FIGS. 7 through 9, the slits 284 in the coupling component 28 and the axial portions 681 of the slits 68 in the inner sleeve 67 are situated in a plane. The locking device 48 can therefore be freely pushed by axial movement of the transmission rod 40 between the assembly position 483 shown in FIGS. 3 and 7, the working position 482 shown in FIGS. 4 and 8, and the working position 481 shown in FIGS. 5 and 9. In particular in the sections along the plane A-A in FIGS. 8 and 9, it can be recognized how the locking device 48 in the working positions 482, 481 by form locking prevents a relative rotation of the coupling component 28 and the inner sleeve 67.

FIGS. 10 and 11 show schematic sectional views of an additional embodiment of the tool 20 described above with reference to FIGS. 1 and 2. The sectional planes of FIGS. 10 and 11 are parallel to the planes of projection of FIGS. 1 and 2, correspond to the sectional planes of FIGS. 3 through 5, and contain the longitudinal axis 29 of the tool 20. The embodiment in FIGS. 10 and 11 resembles the embodiment introduced above with reference to FIGS. 3 through 9 in a few features, in particular those of the rotation bearing 60 and of the coupling device 70; reference is hereby made to their description above, supported by FIGS. 3 through 9. The embodiment in FIGS. 10 and 11 is distinguished from the embodiment in FIGS. 3 through 9, in particular in the configuration of the jaw members 25, 26.

In the embodiment in FIGS. 10 and 11, only the first jaw member 25 can be pivoted around an axis defined by an axle 232 between the prongs 231 of the joint device 23, perpendicular to the plane of projection of FIGS. 10 and 11. The second jaw member 26 is rigidly connected with the joint device 23 by the prongs 231; in particular it is configured as a single unit with the joint device 23. A lever 254 is rigidly connected on an end portion with the first jaw member 25 close to the axle 232 and mechanically coupled with the transmission rod 40 on the other end portion via a joint 255. A translational movement of the transmission rod 40 is translated by the lever 254 into a pivot movement of the first jaw member 25 about the axis defined by the axle 232 and vice versa. In the area of the joint device 23, the transmission rod 40 has a pliability that is required to allow a movement of the joint 255 on an arc segment about the pivot axis of the first jaw member 25 defined by the axle 232.

FIG. 10 shows the first jaw member 25 in a fully open position 253 and the locking device 48 in an assembly position 483. In FIG. 11 the first jaw member is shown in a closed position 251 and the locking device 48 in a working position 481. To this extent the depictions of FIGS. 3 and 10 and those of FIGS. 5 and 11 correspond to one another. With the locking device 48 in the assembly position 483 shown in FIG. 10, the tool 20 can be affixed to the distal end portion 31 of the shaft 30 or can be removed from it. With the locking device 48 in the working position 481 shown in FIG. 11 and in other working positions situated between the working position 481 and the assembly position 483, the mechanical coupling between the tool 20 and the distal end portion 31 of the shaft 30 is locked in the coupling device 70.

In all positions of the first jaw member 25 and in all corresponding positions of the locking device 48, the rotation bearing 60 on the distal end portion 31 of the shaft 30 allows a rotation of the sleeve device formed by the sleeves 65, 67 and the tool 20 coupled with it together with the transmission rod 40 in relation to the shaft tube 301 of the shaft 30 about the longitudinal axis 29 of the tool 20. This rotation can, in particular, be powered by the rotary wheel 57 shown in FIGS. 1 and 2 on the handling device 50 on the proximal end portion 12 of the micro-invasive surgical instrument 10.

On the jaw members 25, 26, profiled hard metal plates 259, 269 are provided that, contrary to the depictions in FIGS. 3 through 5, can be provided also in the embodiment shown there. The hard metal plates 259, 269 with their profiling can contribute toward preventing an object grasped by the jaw members 25, 26 from slipping away. The use of a hard material for the hard metal plates 259, 269 reduces the wear and allows—especially in the case of a polished surface—easy removal of residues or impurities.

FIGS. 12 and 13 show schematic depictions of an additional embodiment of the tool 20 and of the distal end portion 31 of the shaft of the micro-invasive surgical instrument 10 introduced above with reference to FIGS. 1 and 2. FIG. 12 shows a schematic depiction of a section along a plane that is parallel to the planes of projection of FIGS. 1 and 2, corresponds to the sectional planes of FIGS. 3 through 5, 10 and 11, and contains the longitudinal axis 29 of the tool 20. FIG. 13 shows a schematic depiction that resembles the one in FIG. 12. Unlike in FIG. 12, however, in FIG. 13 not all interfaces are hatched and not all hatched surfaces are interfaces.

The embodiment in FIGS. 12 and 13 resembles in some features the embodiment in FIGS. 3 through 9 and in particular the embodiment in FIGS. 10 and 11. The embodiment in FIGS. 12 and 13 is distinguished from the embodiment in FIGS. 10 and 11 in particular in that on the distal end portion 307 of the shaft tube 301 a collar component 63 is affixed on whose distal end portion a ring-shaped collar 64 is provided that extends radially outward. The outer sleeve 65 on its proximal border comprises a collar 66 that extends radially inward and that engages in a flat ring-shaped groove of corresponding cross-section between the distal end of the shaft tube 301 and the collar 64 that extends radially outward on the collar component 63. The collar 64 extending radially outward on the distal border of the collar component 63 engages in a ring-shaped groove of corresponding cross-section between the collar 66 extending radially inward on the proximal border of the outer sleeve 65 and the proximal border of the inner sleeve 67.

The collars 64, 66 and the grooves into which the collars 64, 66 engage are, similarly as with the embodiments in FIGS. 3 through 11, adjusted to one another with respect to their cross-sections in such a way that they provide a form-locked connection, with minor play and friction, between the sleeve component formed by the sleeves 65, 67 and the shaft tube 301 and simultaneously form a rotation bearing. The aforementioned rotation bearing allows a rotation of the component formed from the sleeves 65, 67 with respect to the shaft tube 301 about the longitudinal axis 29 of the tool 20.

The embodiment in FIGS. 12 and 13 is distinguished from the embodiments in FIGS. 3 through 11, in addition, in that it is configured for a bipolar electro-surgical application in which an electric current or an electric field can be generated between the jaw members 25, 26. For this purpose the transmission rod 40 comprises an insulating mantle 422 of an electrically insulating material, which electrically insulates the transmission rod 40 with respect to the shaft tube 301, the collar component 63, the coupling component 28 and the joint device 23. For the purpose of electrical insulation, the locking device 48 is produced in an electrically insulating material and/or—as indicated in FIGS. 12 and 13—is configured with a ring-shaped portion 480. The ring-shaped portion 480 surrounds the transmission rod 40 and its insulating mantle 422 and is joined to the insulating mantle 422 in particular by force-locking, form-locking and/or firm bonding. In particular, the ring-shaped portion 480 of the locking device 48, owing to form-locking with the insulating mantle 422, cannot be slid with respect to it, at least in the direction parallel to the longitudinal axis 29 of the tool 20.

In addition, the coupling component 28 comprises spring tongues 287 with contacts 288, which extend to the collar component 63. The contacts 288 are pressed by electrical forces of the spring tongues 287 onto a corresponding circular-ring-shaped contact surface on the collar component 63. By the spring tongues 287 and contacts 288, the coupling component 28 and thus also the joint device 23 and the second jaw member 26 are electrically conductively connected with the collar component 63 and by it with the shaft tube 301.

FIG. 13 shows a schematic depiction resembling the depiction in FIG. 12. Unlike FIG. 12, however, FIG. 13 is not a pure sectional depiction. In FIG. 13, not all interfaces are hatched and not all hatched surfaces are interfaces. Rather, the insulating mantle 422 of the transmission rod 40 is not hatched; the first jaw member 25 and all components connected electrically conductively with it in the direction from left below to right above are shown hatched and the second jaw member 26 and all components connected electrically conductively with it from right below to left above are shown hatched. In addition, a current path 75 to the first jaw member 25 and a current path 76 to the second jaw member 26 are indicated, which are marked with arrows in opposite directions for intuitive differentiation. The current path 75 leads to the first jaw member 25 by way of the transmission rod 40, the joint 255 between the transmission rod 40 and the lever 254, and the lever 254. The current path 76 leads to the second jaw member 26 by way of the shaft tube 301, the collar component 63, the contacts 288, spring tongues 287 and other areas of the coupling component 28, the joint device 23 with the prongs 231. The outer sleeve 65 and the inner sleeve 67 are also parallel in the current path 76 to the second jaw member 26.

What is claimed is:

1. A shaft for a micro-invasive surgical instrument, said shaft being configured to detachably mechanically couple with a surgical tool, said shaft having:
   a shaft tube with a proximal end portion and a distal end portion;
   a rotation bearing positioned at the distal end portion of the shaft tube; and
   a coupling device comprising a groove or slit, the coupling device detachably mechanically coupling the rotation bearing at the distal end portion of the shaft tube with a body of the surgical tool upon insertion of a cam on said surgical tool into the groove or slit, the groove or slit having an axial portion extending along a longitudinal axis of the coupling device and a peripheral portion extending along a perimeter of the coupling device, the axial portion and the peripheral portion requiring relative movement between the rotation bearing and the surgical tool for detachably mechanically coupling the rotation bearing at the distal end portion of the shaft tube with the body of the surgical tool;

wherein the rotation bearing is configured to allow rotation of the coupling device with respect to the shaft tube about a longitudinal axis of the distal end portion of the shaft tube; and wherein the rotation bearing is a Radiax bearing, and a proximal portion of the coupling device forms a first portion of the Radiax bearing, and a second portion of the Radiax bearing surrounds the distal end portion of the shaft tube and the first portion of the Radiax bearing.

2. The shaft according to claim 1, wherein the rotation bearing includes a collar extending radially inward and a collar extending radially outward, such that either the collar extending radially outward is rigidly connected with the coupling device and the collar extending radially inward is rigidly connected with the distal end portion of the shaft tube, or vice versa.

3. The shaft according to claim 1, wherein the shaft is curved.

4. The shaft according to claim 1, wherein the coupling device is configured for a locking capacity of the detachable mechanical coupling with the surgical tool.

5. The shaft according to claim 1, in addition having:
a sleeve component with a distal portion that forms a part of the coupling device and a proximal portion that forms a part of the rotation bearing.

6. A micro-invasive surgical instrument having:
a shaft tube with a proximal end portion and a distal end portion;
a rotation bearing positioned at the distal end portion of the shaft tube;
a surgical tool with a proximal end having a cam; and
a coupling device comprising a groove or slit, the coupling device detachably mechanically coupling the rotation bearing at the distal end portion of the shaft tube with a body of the surgical tool upon insertion of the cam on said surgical tool into the groove or slit, the groove or slit having an axial portion extending along a longitudinal axis of the coupling device and a peripheral portion extending along a perimeter of the coupling device, the axial portion and the peripheral portion requiring relative movement between the rotation bearing and the surgical tool for detachably mechanically coupling the rotation bearing at the distal end portion of the shaft tube with the body of the surgical tool;

wherein the rotation bearing is configured to allow rotation of the coupling device with respect to the shaft tube about a longitudinal axis of the distal end portion of the shaft tube;

wherein the rotation bearing is a Radiax bearing, and a proximal portion of the coupling device forms a first portion of the Radiax bearing, and a second portion of the Radiax bearing surrounds the distal end portion of the shaft tube and the first portion of the Radiax bearing.

7. The micro-invasive surgical instrument according to claim 6, in addition having:
a handling device, which is coupled with the proximal end portion of the shaft, such that the handling device comprises an actuation device to rotate a transmission rod that is positioned in the shaft and whose distal end portion is coupled with the surgical tool.

8. The micro-invasive surgical instrument according to claim 6, wherein the surgical tool has a locking device to lock the coupling of the rotation bearing at the distal end portion of the shaft tube with the body of the surgical tool and inhibit relative movement between the coupling device and the surgical tool.

9. The micro-invasive surgical instrument according to claim 8, wherein the locking device comprises a pin and a cap disposed at one end of the pin, the locking device being positionable within the axial portion of the groove or slit.

10. The micro-invasive surgical instrument according to claim 9, wherein a cylindrical portion of the pin is disposed in the transmission rod in a borehole, said borehole is oriented perpendicular to a longitudinal axis of the surgical tool.

* * * * *